(12) United States Patent
Cadieux, Jr.

(10) Patent No.: US 9,381,545 B2
(45) Date of Patent: Jul. 5, 2016

(54) ON-LINE OIL AND FOREIGN MATTER DETECTION SYSTEM AND METHOD

(71) Applicant: Altria Client Services Inc., Richmond, VA (US)

(72) Inventor: Edmond J. Cadieux, Jr., Mechanicsville, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 14/745,126

(22) Filed: Jun. 19, 2015

(65) Prior Publication Data

US 2015/0290684 A1    Oct. 15, 2015

Related U.S. Application Data

(63) Continuation of application No. 13/842,512, filed on Mar. 15, 2013, now Pat. No. 9,073,091.

(51) Int. Cl.
*B07C 5/02* (2006.01)
*B07C 5/342* (2006.01)
(Continued)

(52) U.S. Cl.
CPC . *B07C 5/342* (2013.01); *A24B 1/04* (2013.01); *B07C 5/3427* (2013.01); *B07C 5/366* (2013.01);
(Continued)

(58) Field of Classification Search
CPC .......... B07C 5/34; B07C 5/342; B07C 5/3416
USPC ...................... 209/3, 3.3, 576, 587
See application file for complete search history.

(56) References Cited

U.S. PATENT DOCUMENTS

| 3,085,581 A | 4/1963 | Rosenberg et al. |
| 3,417,241 A | 12/1968 | Davis |

(Continued)

FOREIGN PATENT DOCUMENTS

| DE | 20320957 U1 | 7/2005 |
| DE | 102011007666 A1 | 10/2012 |

(Continued)

OTHER PUBLICATIONS

International Search Report of International Application No. PCT/US2014/026556 dated Aug. 5, 2014.

(Continued)

*Primary Examiner* — Terrell Matthews
(74) *Attorney, Agent, or Firm* — Roberts Mlotkowski Safran & Cole, P.C.

(57) ABSTRACT

A system for detecting oil contaminated product and foreign matter within a product stream is provided. The system includes a first conveying means for delivering a product stream; a first detection apparatus for detecting oil contaminated product, the first detection apparatus positioned proximate the product stream, the first detection apparatus including a high intensity infrared light source directed at the product stream; and a high speed NIR spectrometer sensor tuned to detect a reflected signal from a taggant disposed in the oil of the oil contaminated product; a second detection apparatus for detecting foreign matter within a product stream, the second detection apparatus positioned proximate the product stream, the second detection apparatus including a light source for illuminating the product stream and a detector for detecting light reflected from the product stream; and a controller for determining whether the product stream contains oil contaminated product or foreign matter by monitoring signals obtained from the first detection apparatus and the second detection apparatus.

10 Claims, 6 Drawing Sheets

(51) Int. Cl.

| | | |
|---|---|---|
| *A24B 1/04* | (2006.01) | |
| *B07C 5/36* | (2006.01) | |
| *C10L 1/00* | (2006.01) | |
| *G01N 21/359* | (2014.01) | |
| *G01N 21/55* | (2014.01) | |
| *G01N 21/64* | (2006.01) | |
| *G01N 21/85* | (2006.01) | |
| *G01N 21/94* | (2006.01) | |
| *G01N 21/952* | (2006.01) | |
| *G01N 21/84* | (2006.01) | |

(52) U.S. Cl.
CPC .............. *C10L 1/003* (2013.01); *G01N 21/359* (2013.01); *G01N 21/55* (2013.01); *G01N 21/643* (2013.01); *G01N 21/85* (2013.01); *G01N 21/94* (2013.01); *C10N 2240/56* (2013.01); *G01N 21/952* (2013.01); *G01N 2021/646* (2013.01); *G01N 2021/6439* (2013.01); *G01N 2021/845* (2013.01); *G01N 2021/8411* (2013.01); *G01N 2021/8592* (2013.01)

(56) References Cited

U.S. PATENT DOCUMENTS

| | | | |
|---|---|---|---|
| 3,806,727 A | 4/1974 | Leonard et al. | |
| 3,812,349 A | 5/1974 | Gugliotta et al. | |
| 3,880,289 A * | 4/1975 | Gray | B07C 5/3425 |
| | | | 209/565 |
| 3,985,582 A | 10/1976 | Bibring et al. | |
| 4,175,996 A | 11/1979 | Battard et al. | |
| 4,445,520 A | 5/1984 | Knight et al. | |
| 4,480,702 A | 11/1984 | Kelly, Jr. | |
| 4,657,144 A * | 4/1987 | Martin | A24B 1/04 |
| | | | 131/108 |
| 4,845,374 A | 7/1989 | White et al. | |
| 4,858,465 A | 8/1989 | Molina | |
| 4,971,077 A | 11/1990 | Dominguez et al. | |
| 5,048,543 A | 9/1991 | Smith | |
| 5,092,349 A | 3/1992 | Smith et al. | |
| 5,134,291 A | 7/1992 | Ruhl, Jr. et al. | |
| 5,265,732 A | 11/1993 | Long | |
| 5,440,919 A | 8/1995 | Cooper | |
| 5,462,176 A | 10/1995 | Hereford et al. | |
| 5,476,108 A | 12/1995 | Dominguez et al. | |
| 5,525,516 A | 6/1996 | Krutak et al. | |
| 5,554,408 A | 9/1996 | Cain et al. | |
| 5,554,480 A | 9/1996 | Patel et al. | |
| 5,665,538 A | 9/1997 | Slater et al. | |
| 5,715,843 A | 2/1998 | Hapke et al. | |
| 5,764,874 A | 6/1998 | White | |
| 5,807,605 A | 9/1998 | Tingey et al. | |
| 5,887,073 A | 3/1999 | Fazzari et al. | |
| 5,974,860 A * | 11/1999 | Kuroda | G01M 3/38 |
| | | | 250/301 |
| 5,990,197 A | 11/1999 | Escano et al. | |
| 6,025,200 A | 2/2000 | Kaish et al. | |
| 6,058,940 A | 5/2000 | Lane | |
| 6,060,677 A | 5/2000 | Ulrichsen et al. | |
| 6,064,032 A | 5/2000 | Voss et al. | |
| 6,135,386 A | 10/2000 | Garthaffner | |
| 6,149,719 A | 11/2000 | Houle | |
| 6,166,366 A | 12/2000 | Lewis et al. | |
| 6,380,547 B1 | 4/2002 | Gonzalez et al. | |
| 6,384,359 B1 | 5/2002 | Belcastro et al. | |
| 6,477,227 B1 | 11/2002 | Kaiser et al. | |
| 6,511,756 B1 | 1/2003 | Obuchi et al. | |
| 6,529,273 B1 | 3/2003 | Norris et al. | |
| 6,633,043 B2 | 10/2003 | Hegazi et al. | |
| 6,734,383 B1 | 5/2004 | Calcoen et al. | |
| 6,771,365 B1 * | 8/2004 | Pirani | G01N 21/8915 |
| | | | 356/238.2 |
| 6,795,179 B2 | 9/2004 | Kumar | |
| 6,809,819 B1 * | 10/2004 | Vinjamoori | G01N 21/53 |
| | | | 356/337 |
| 6,830,310 B2 | 12/2004 | Iu et al. | |
| 6,905,538 B2 | 6/2005 | Auslander | |
| 6,914,678 B1 | 7/2005 | Ulrichsen et al. | |
| 6,926,764 B2 | 8/2005 | Bleikolm et al. | |
| 7,142,296 B2 | 11/2006 | Cunningham et al. | |
| 7,153,557 B2 | 12/2006 | Rancien | |
| 7,157,611 B2 | 1/2007 | Banavali et al. | |
| 7,227,148 B2 | 6/2007 | Sato et al. | |
| 7,256,398 B2 | 8/2007 | Ross et al. | |
| 7,319,039 B2 | 1/2008 | Sullivan | |
| 7,378,675 B2 | 5/2008 | Ross et al. | |
| 7,391,035 B2 | 6/2008 | Kong et al. | |
| 7,488,945 B2 | 2/2009 | Li et al. | |
| 7,538,324 B2 | 5/2009 | Deevi et al. | |
| 7,705,144 B2 | 4/2010 | Holmes | |
| 7,749,438 B2 | 7/2010 | Zeinali et al. | |
| 7,767,457 B2 | 8/2010 | Mun et al. | |
| 7,768,643 B1 | 8/2010 | Janssens et al. | |
| 7,800,088 B2 | 9/2010 | Ross et al. | |
| 7,816,616 B2 * | 10/2010 | Kenny | B07C 5/342 |
| | | | 209/576 |
| 7,829,162 B2 | 11/2010 | Eskra et al. | |
| 7,842,896 B1 | 11/2010 | Calcoen et al. | |
| 7,938,124 B2 | 5/2011 | Izumiya et al. | |
| 7,985,590 B2 | 7/2011 | McNeil | |
| 8,415,165 B2 | 4/2013 | Liang et al. | |
| 8,641,933 B2 | 2/2014 | Purdy et al. | |
| 8,692,148 B1 * | 4/2014 | Sommer, Jr. | B07C 5/368 |
| | | | 209/576 |
| 9,006,599 B2 * | 4/2015 | Adams | B07C 5/342 |
| | | | 209/577 |
| 9,080,987 B2 | 7/2015 | Faenza | |
| 2001/0045378 A1 | 11/2001 | Charles et al. | |
| 2002/0074269 A1 | 6/2002 | Hensley et al. | |
| 2002/0094058 A1 | 7/2002 | Kaiser et al. | |
| 2003/0034282 A1 | 2/2003 | Safai | |
| 2003/0058990 A1 | 3/2003 | Kaiser et al. | |
| 2003/0097833 A1 | 5/2003 | Ingram et al. | |
| 2003/0129283 A1 | 7/2003 | Martinez Carballido | |
| 2003/0141459 A1 | 7/2003 | Hegazi et al. | |
| 2003/0183326 A1 | 10/2003 | O'Connor | |
| 2003/0194052 A1 | 10/2003 | Price et al. | |
| 2004/0134504 A1 | 7/2004 | Lane | |
| 2005/0031838 A1 * | 2/2005 | Lagunowich | B41M 3/144 |
| | | | 428/211.1 |
| 2005/0092336 A1 | 5/2005 | Zielke et al. | |
| 2005/0236015 A1 | 10/2005 | Goel et al. | |
| 2005/0276906 A1 | 12/2005 | Metzger | |
| 2006/0016735 A1 | 1/2006 | Ito et al. | |
| 2006/0081503 A1 | 4/2006 | Wegner | |
| 2006/0118741 A1 | 6/2006 | Ross et al. | |
| 2006/0131518 A1 | 6/2006 | Ross et al. | |
| 2006/0246020 A1 | 11/2006 | Cole et al. | |
| 2006/0262318 A1 | 11/2006 | Sullivan | |
| 2006/0291872 A1 | 12/2006 | Mei et al. | |
| 2007/0023715 A1 | 2/2007 | Ross et al. | |
| 2007/0048761 A1 | 3/2007 | Reep et al. | |
| 2007/0084269 A1 | 4/2007 | Quest et al. | |
| 2007/0187617 A1 | 8/2007 | Kong et al. | |
| 2008/0030712 A1 | 2/2008 | Tokhtuev et al. | |
| 2009/0047531 A1 | 2/2009 | Bartley et al. | |
| 2009/0097833 A1 | 4/2009 | Imada | |
| 2009/0104711 A1 * | 4/2009 | Sim | C09K 11/06 |
| | | | 436/172 |
| 2009/0185182 A1 | 7/2009 | Kim et al. | |
| 2009/0280341 A1 | 11/2009 | Maruichi et al. | |
| 2009/0321623 A1 | 12/2009 | Ross et al. | |
| 2010/0080456 A1 | 4/2010 | Paul et al. | |
| 2010/0219377 A1 | 9/2010 | Ebert | |
| 2010/0224795 A1 | 9/2010 | Cole et al. | |
| 2010/0226861 A1 | 9/2010 | Cole et al. | |
| 2010/0233447 A1 | 9/2010 | Campbell | |
| 2010/0290040 A1 | 11/2010 | Berghmans | |
| 2011/0141272 A1 | 6/2011 | Uto et al. | |
| 2011/0151576 A1 | 6/2011 | Perfect et al. | |
| 2011/0168915 A1 | 7/2011 | Yajima et al. | |
| 2011/0216190 A1 | 9/2011 | Shimazu et al. | |

(56) References Cited

U.S. PATENT DOCUMENTS

| | | |
|---|---|---|
| 2012/0104278 A1 | 5/2012 | Downing et al. |
| 2012/0267287 A1 | 10/2012 | Bailey |
| 2012/0302474 A1* | 11/2012 | Faenza .................. B07C 5/342 508/296 |
| 2013/0082173 A1 | 4/2013 | Cadieux et al. |
| 2013/0179090 A1 | 7/2013 | Conroy et al. |
| 2013/0188170 A1 | 7/2013 | Wilkins |
| 2013/0320216 A1* | 12/2013 | Aiko .................. G01B 11/303 250/349 |
| 2013/0320237 A1 | 12/2013 | Cadieux et al. |
| 2014/0262966 A1 | 9/2014 | Cadieux, Jr. |
| 2015/0008162 A1 | 1/2015 | Cadieux, Jr. |
| 2015/0048250 A1 | 2/2015 | Cadieux, Jr. et al. |
| 2015/0290684 A1 | 10/2015 | Cadieux, Jr. |
| 2015/0315511 A1 | 11/2015 | Faenza |
| 2015/0323459 A1 | 11/2015 | Cadieux, Jr. |

FOREIGN PATENT DOCUMENTS

| | | |
|---|---|---|
| EP | 0146299 A1 | 6/1985 |
| EP | 0223446 A2 | 5/1987 |
| EP | 657028 A1 | 6/1995 |
| EP | 0897762 A2 | 2/1999 |
| GB | 2091416 | 7/1982 |
| JP | S61-290057 A | 12/1986 |
| JP | S64-059095 A | 3/1989 |
| JP | H06-066728 A | 3/1994 |
| JP | 2002-505426 A | 2/2002 |
| JP | 2002-513155 A | 5/2002 |
| WO | 9117265 A1 | 11/1991 |
| WO | 9800243 A1 | 1/1998 |
| WO | 9957414 A2 | 11/1999 |
| WO | 0125747 A2 | 4/2001 |
| WO | 0125748 A2 | 4/2001 |
| WO | 0125764 A1 | 4/2001 |
| WO | 0125766 A1 | 4/2001 |
| WO | 0125767 A1 | 4/2001 |
| WO | 0125820 A2 | 4/2001 |
| WO | 02068945 A1 | 9/2002 |
| WO | 2008049515 A2 | 5/2008 |
| WO | 2010007390 A1 | 1/2010 |
| WO | 2012030988 A1 | 3/2012 |
| WO | 2012050844 A1 | 4/2012 |
| WO | 2012162701 A1 | 11/2012 |
| WO | 2013181286 A1 | 12/2013 |
| WO | 2014168720 A1 | 10/2014 |

OTHER PUBLICATIONS

International Search Report of International Application No. PCT/US2012/039870 dated Aug. May 26, 2011.

International Search Report of International Application No. PCT/US2013/043172 dated Aug. 6, 2013.

Victoria B. Rodriguez et al., "Encapsulation and stabilization of indocyanine green within poly (styrene-alt-maleic anhydride) block-poly (styrene) micelles for near-infrared imaging" Journal of Biomedical Optics, SPIE—International Society for Optical Engineering,vol. 13 No. 1, Jan. 30, 2008, p. 14025-1-140025-10; XP002664215.

International Preliminary Report on Patentability of International Application No. PCT/US2014/026556 dated Sep. 15, 2015.

International Preliminary Report on Patentability of International Application No. PCT/US2013/0043172 dated Dec. 2, 2014.

International Preliminary Report on Patentability of International Application No. PCT/US2012/039870 dated Nov. 26, 2013.

* cited by examiner

ON-LINE OIL AND FOREIGN MATTER DETECTION SYSTEM AND METHOD

This application is a continuation of U.S. application Ser. No. 13/842,512, filed on Mar. 15, 2013, the contents of which are hereby incorporated by reference.

FIELD

Disclosed herein is an on-line system and method for the detection and separation of unwanted materials and/or oil contaminated product.

ENVIRONMENT

Tobacco delivered for processing into filler for cigarettes may occasionally contain foreign matter such as pieces of the container in which it is shipped and/or stored, bits of string and paper, and other items. There remains a need for methods and systems to remove foreign, non-tobacco related materials (NTRM or foreign material).

Another area where it is important to optically inspect and sort a moving stream of product is in the food-processing industry where there is a need to automatically sort food products by optical inspection of the food products to identify food articles having undesirable visual characteristics or intermixed foreign material. Examples include fruits, vegetables, baked products, nuts and the like. Other areas requiring a similar sorting of products or articles includes the sorting of naturally occurring products such as meat products, particularly of quartered or cubed poultry or beef products. In the processing and packaging of comestible consumer products and products designed to provide tobacco enjoyment, oils, greases and lubricants may come into contact with the product being produced.

In the case of products designed to provide tobacco enjoyment, tobacco leaf may be contacted by machinery during harvesting, curing and transport to a stemmery. When leaf is provided in strip form at a stemmery, and cut or otherwise shredded to the desired size, while unlikely, oils, greases and lubricants can come into contact with the tobacco. Likewise, lubricants used in operating the various machines used in the processing of the tobacco can come into contact with that tobacco. The sources of lubricant contamination can vary, such as when a particular piece of machinery or component of that piece of machinery fails to operate in an optimum fashion.

Although extremely unlikely, lubricants may come into contact with tobacco due to leakage of lubricants through gaskets or seals, from sliding mechanisms, from drum systems, from gear boxes, from pumps, from sealed rolling bearing units, from chains and belts, and the like. Lubricants are used in conditioning cylinders, threshers, separators, redryers, receivers, feeders, conveyors, cutters, blenders, tobacco presses and other such pieces of equipment that are commonly used in tobacco stemmeries and in tobacco primary processing operations.

Since lubricants of similar compositions are used throughout the various stages of tobacco treatment and cigarette manufacture, it is often difficult for the cigarette manufacturer to locate the source of a particular lubricant. As such, the cigarette manufacturer is forced to conduct a time consuming search for the source of the lubricant.

None of the commercially available optical scanning and sorting systems can detect and reject oil-contaminated product. As such, it would be advantageous if the inspection for oils, greases, lubricants, NTRM and other undesirable materials on or intermixed with consumer products, such as food, tobacco and tobacco products could be conducted on-line, that is, in real time, using an optical scanning and sorting system during the production process.

SUMMARY

In one aspect, a system for detecting oil contaminated product and foreign matter within a product stream is provided. The system includes a first conveying means for delivering a product stream; a first detection apparatus for detecting oil contaminated product, the first detection apparatus positioned proximate the product stream, the first detection apparatus including a high intensity infrared light source directed at the product stream; and a high speed NIR spectrometer sensor tuned to detect a reflected signal from a taggant disposed in the oil of the oil contaminated product; a second detection apparatus for detecting foreign matter within a product stream, the second detection apparatus positioned proximate the product stream, the second detection apparatus including a light source for illuminating the product stream and a detector for detecting light reflected from the product stream; and a controller for determining whether the product stream contains oil contaminated product or foreign matter by monitoring signals obtained from the first detection apparatus and the second detection apparatus.

In one form, the system includes at least one deflecting system responsive to the signals obtained from the first detection apparatus and/or the second detection apparatus, the at least one deflecting system directing fluid under pressure at a portion of the product stream when the controller determines that foreign matter or oil contaminated product is present in the product stream.

In another form, the fluid so directed is effective to remove the foreign matter or oil contaminated product.

In yet another form, the system includes a second conveying means located below and spaced vertically from the first conveying means for further conveying the product stream from the first conveying means, wherein the product stream is transferred from the first conveying means to the second conveying means by falling therebetween under the influence of gravity in a cascade.

In still yet another form, the fluid is a gas, which may be air.

In a further form, the taggant is a fluorescent Stokes-shifting taggant, which absorbs radiation at a first wavelength and emits radiation at a second wavelength, different from the first wavelength.

In a still further form, the first wavelength is about 760 to about 810 nanometers and the second wavelength is about 810 nanometers to about 960 nanometers.

In a still yet further form, the first wavelength is about 805 nanometers and the second wavelength is about 840 nanometers.

In another form, the taggant is oil soluble. The irradiated product absorbs the original radiation and re-emits radiation of a different wavelength than the original radiation, which then may be detected as disclosed herein.

In another aspect, a method for removing oil contaminated product and foreign matter within a product stream is contemplated and provided herein. The method includes the steps of adding a fluorescent taggant to oil or lubricant contained in at least one processing machine; conveying a product stream that has been processed by the at least one processing machine; irradiating the conveyed product stream with infrared radiation; detecting infrared radiation emitted from the irradiated product stream due to the presence of the fluorescent taggant and generating a first signal in response thereto;

illuminating the conveyed product stream; detecting light reflected from the illuminated product stream; comparing the light reflected from the illuminated product stream with light that would be expected to be reflected from an illuminated product stream free of foreign matter, and generating a second signal when the reflected light indicates the presence of foreign matter; and removing a portion of the conveyed product stream in response to the first or second signal.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-6, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

The detection and separation system of the present invention can be used in many processes and for consumer products which are susceptible to lubricant contamination or the presence of unwanted materials during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, lumber or any other manufactured or packaged product wherein an absence of oil is desired.

Figure 1:
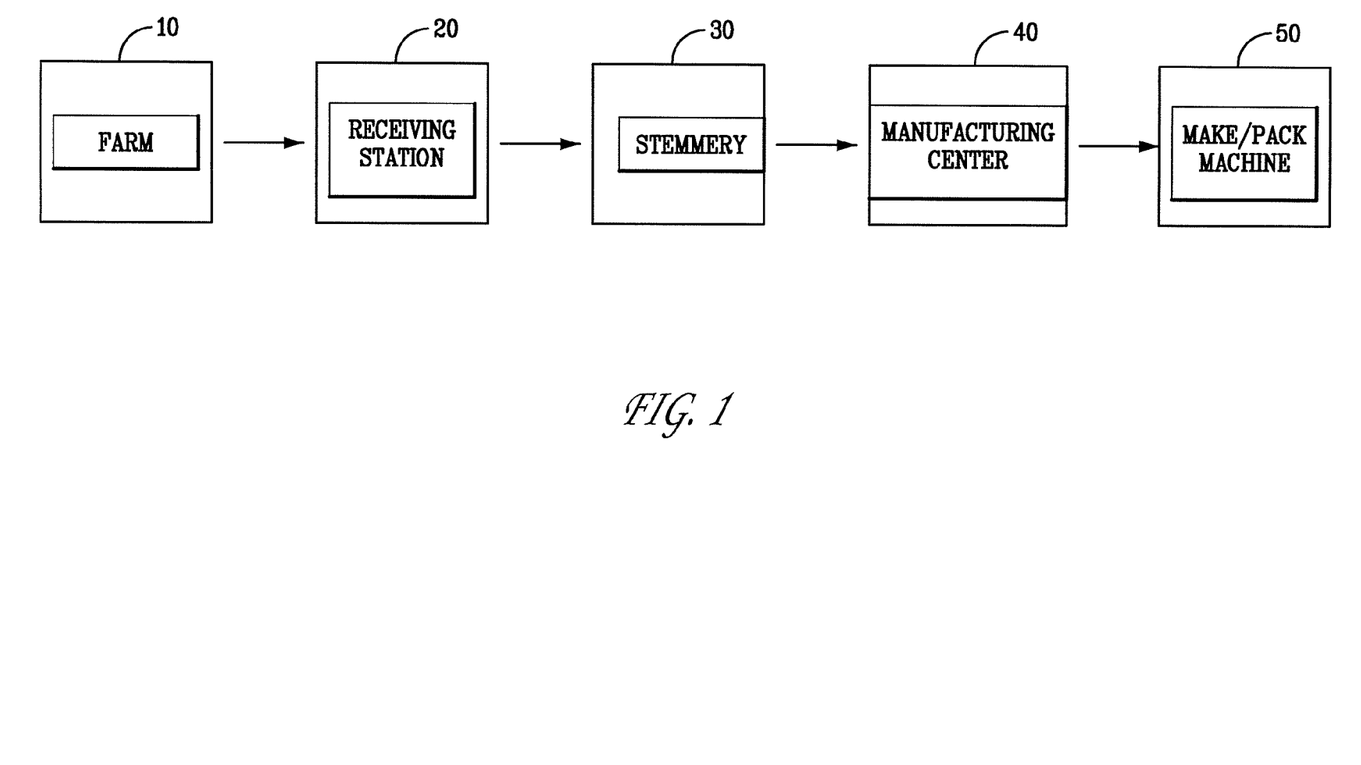
FIG. 1 is a block diagram showing the various stages in the process of cigarette manufacturing.

Referring now to FIG. 1, a block diagram showing the various stages in the process of cigarette manufacturing is presented. As shown. Tobacco is first harvested at farm 10, which, in the case of tobacco for use in cigarette manufacturing or the production of moist smokeless tobacco (MST), will be harvested at least in part by machinery. Tobacco in the form of leaf is baled and received at a receiving station 20 from farm 10. Again, the opportunity exists for the tobacco bale to come in contact with lubricated machinery at receiving station 20. The baled tobacco may be transferred to a stemmery 30 wherein large stems are removed by machines to produce destemmed tobacco. The destemmed tobacco is packed into bales which are then stored for a suitable time period of up to several years. Destemmed tobacco is then transferred to manufacturing center 40, wherein various types of tobacco strip may be machine blended according to a predetermined recipe. The blended tobacco may be treated by adding various flavorants to provide a cased tobacco, which is cut at 20-40 cuts per inch to provide tobacco "cut filler." Various other types of tobacco can be added to the cut filler including puffed tobacco, reconstituted tobacco, tobacco reclaimed from rejected cigarettes, and the like, to provide a final product blend. The blend may be then fed to make/pack machine 50, which includes a continuous cigarette rod making apparatus. The continuous rod is then cut, optionally tipped, and packed, typically through the use of high-speed machinery.

As may be appreciated from the above description, in tobacco processing, tobacco comes into contact with machinery at many different points in the overall process, such as machinery used during the growing and harvesting operations on the farm, handling equipment at the receiving station or auction house, machinery in the stemmery, on conveyors, conditioners, cutters and silos in the primary manufacturing centers, and ultimately on makers, tippers and packers in the make/pack manufacturing centers. By utilizing a different taggant in the lubricants at each of these locations, the discrete source and/or location of contamination can be readily determined by inspection/detection of the finished product.

Figure 2:
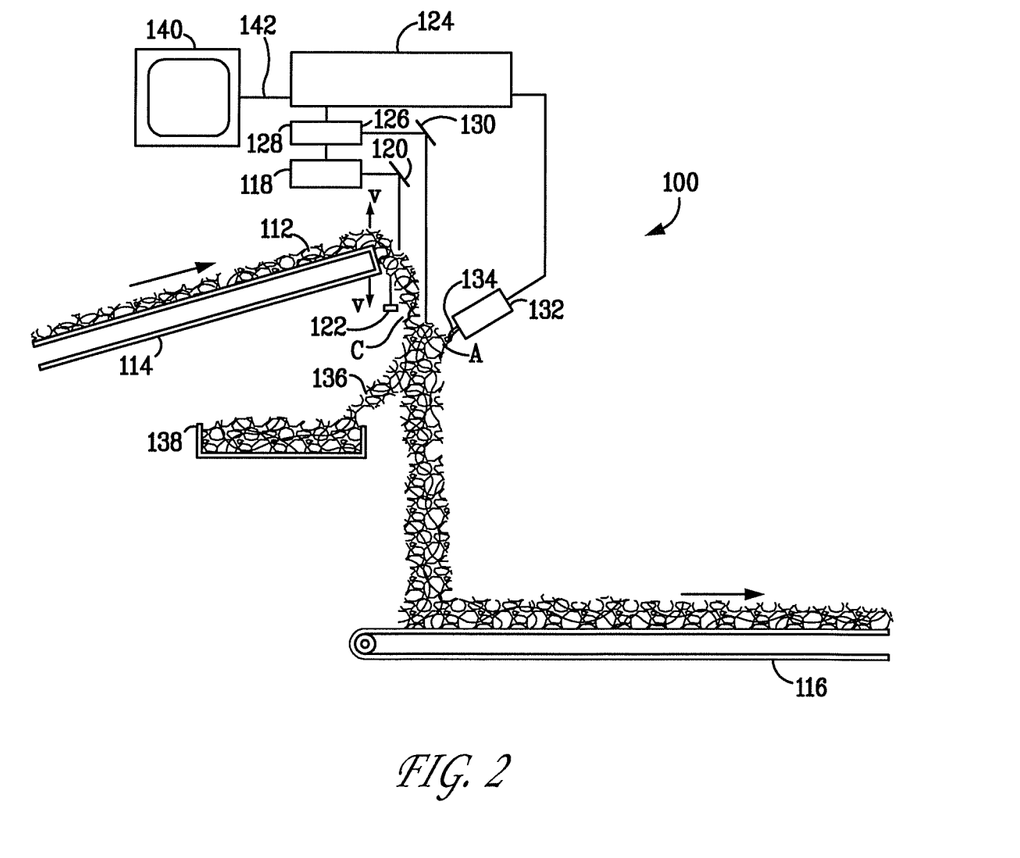
FIG. 2 presents a schematic representation of a detection and separation system, in accordance herewith.

Referring now to FIG. 2, one form of a detection and separation system 100, as disclosed herein, is shown schematically. In operation, a product stream, such as a tobacco stream, 112 containing foreign material, such as foil, cellophane, warehouse tags, and paper, or oil or lubricant contaminated material, is delivered from a processing line by conveyor 114. Conveyor 114 is preferably a vibrating inclined conveyor which vibrates as shown by arrows V. In one form, conveyor 114 ends above another conveyor 116, which can be an ordinary conveyor belt, and is spaced vertically above conveyor 114 a sufficient distance to accommodate the remainder of the system described below. As product stream 112 reaches the end of conveyor 114, it drops under the influence of gravity in a cascade C to conveyor 116. In one form, because conveyor 114 is inclined, the product stream does not have as great a horizontal velocity when it falls, so that cascade C does not have any significant front-to-back horizontal spread.

In another form, detection and separation system 100 may include a single conveyor 114 for inspecting finished product, such as cigarettes, smokeless tobacco containers, SNUS pouches, etc., with product rejection, described in more detail below, taking place on the same conveyor.

Light or electromagnetic radiation having a first wavelength is provided by an optical scanner 118 and is directed toward the cascade C material in the product stream 112 by the mirror 120. Light or electromagnetic radiation that is reflected, refracted or converted by fluorescent or other emission is returned to the mirror 120, and to the optical scanner 118. Some of the light that is not returned interacts with the background element 122, where a portion is returned to the mirror 120, and to the optical scanner 118. These portions returned to the mirror 120 form first, second and third signals.

Light or electromagnetic radiation that is returned from material in the product stream 112 having a wavelength that is longer than the first wavelength is converted into a first signal by the optical scanner 118. Light or electromagnetic radiation having the first wavelength that is reflected by material in the product stream 112 and from the background element 122 is converted into a second signal by the optical scanner 118. Light or electromagnetic radiation having the first wavelength that is scattered by material in the product stream 112 and from the background element 122 is converted into a third signal by the optical scanner 118.

Then, the first, second, and third signals are transformed into a first, second, and third data streams representing the time varying magnitude of each of the signals, and represent the fluorescence channel, reflectance channel, and scatter channel respectively. The data streams are presented to processor 124 and processed.

To detect the presence of oil or lubricant contaminated material in the product stream 112, cascade C is irradiated with IR radiation, which may, as shown, be directed toward the cascade C material in product stream 112 by mirror 130. Radiation emitted by oil or lubricant contaminated material in cascade C of the product stream 112 is returned to the mirror 120, and then to IR detection device 140. As shown in FIG. 1, the source of radiation and the IR detection device may be housed in one unit, although separate units are within the scope of this disclosure. Likewise, other configurations and orientations for irradiating and detecting radiation, with and without mirrors are also contemplated.

In one form, cascade C of the product stream 112 is irradiated with IR radiation at a wavelength of about 805 nm, and instantaneously emits IR radiation at wavelengths at or about 840 nm from any tagged oil which might be contained in product stream. The emitted IR radiation is in turn detected by IR detection device 128, which sends a signal to processor 124 and is processed.

In one form optical detector 118 has a matrix of electro-optical detectors (not shown), which may be a line-scan camera having a lens and a suitable filter, a photomultiplier tube receiver, or other suitable device.

When optical detector 118 detects foreign material, or when IR detection device 140 detects oil or lubricant contaminated material in product stream 112, processor 124 sends a signal to ejector manifold 132, which is positioned in downstream relation to the region illuminated or radiated by optical detector 118 and irradiated by IR detection device 140. Ejector manifold 132 is in fluid transmission relation to the trajectory of the product stream 112. The ejector manifold 132 includes a plurality of ejector nozzles 134, which are individually directed and controlled to selectively remove undesirable product material 136 from the product stream 112. The ejector nozzles 134 act as conduits for directing fluid pulses to dislodge or otherwise re-direct product material traveling in the trajectory. Individual ejector nozzles 134 contained in the ejector manifold 132 are driven by a plurality of removal signals, which may be provided by processor 124.

Ejector nozzles 134 are connected to a source of high pressure fluid which is preferably air at approximately 80 psi, although other gases, such as steam, or liquids, such as water, can be used. When one of ejector nozzles 134 opens in response to a signal, a blast of air A is directed against that portion of cascade C in which the foreign material or oil contaminated material was detected to force that portion 136 of the product stream and/or foreign material to fall into receptacle 138 for manual sorting, if necessary. In the case of non-oil contaminated product, it may be returned to the product processing line upstream or downstream of system 100, depending on whether or not rescanning is desired. Alternatively, portion 136 could be deflected to a conveyor that removes it to another area for processing.

As may be appreciated, system 100 allows tobacco or other materials to be processed at greater rates than a system in which the tobacco or other materials are scanned on a belt conveyer. This is because when product is optically scanned on a belt, it has to be in a "monolayer," or single layer of particles, for all of the particles on the belt to be visible to the optical detector 118. However, as the tobacco or other material falls in cascade C, relative vertical motion between the various particles of tobacco and foreign material is induced by the turbulence of the falling stream, so there is a greater probability that a particular piece of foreign material will be visible to optical detector 118 at some point in its fall. Relative vertical motion also results if the foreign material is significantly lighter or heavier than tobacco so that it has greater or less air resistance as it falls. Relative vertical motion is enhanced by the vibration of conveyor 114 which brings lighter material to the surface of the tobacco before it falls in cascade C, making the lighter material, which is usually foreign material, easier to detect, as in a monolayer.

The inclination of conveyor 114, in reducing the horizontal spread of cascade C as discussed above, also enhances relative vertical motion because the particles in cascade C have little or no horizontal velocity component. Any horizontal velocity component that a particle has when it falls off conveyor 114 is small because conveyor 114 is inclined, and air resistance quickly reduces the horizontal motion to near zero. The relative vertical motion allows a relatively thicker layer of tobacco or other material to be scanned, so that a greater volume can be scanned per unit of scanning area. Given a constant rate of area scanned per unit time, the increased volume scanned per unit area translates into a higher volume of tobacco or other material scanned per unit time.

In one form, system 100, is provided with a user interface 140 that enables an operator (not shown) to observe and control various operational aspects of the system 100. The user interface 140 may include a CRT or LCD panel for output display. For input, the user interface 140 may include a keyboard, touch-screen or other input means known in the art. The operator can view representations of the articles in the product stream 112 as they are processed in system 100 on the user interface 140. Yet further, the user interface 140 provides a means for the operator to configure the operation of system 100 to make a determination between acceptable product and undesirable product. Data gathered by the user interface 140 and provided to the user interface are transported as user interface data 142.

Suitable optics and control circuitry for use with optical detector 118 are disclosed in U.S. Pat. No. 4,657,144, the contents of which are incorporated herein by reference. Other optics and control circuitry are contemplated for use herein and are within the scope of the instant disclosure.

In operation, foreign material is detected by comparing its reflectivity, which depends on a combination of color and surface properties, at a given wavelength to a reference level set above the known reflectivity of tobacco at that wavelength, so that even a particle of foreign material of the same color as tobacco will be detected if its reflectivity is higher than that of tobacco. The optical detector 118 is sensitive to light with a wavelength in the range of from about 200 nm to about 1300 nm. The sensitivity of optical detector 118 to a particular foreign material or group of foreign materials can be enhanced by using filters and windows which transmit those wavelengths that are preferentially reflected by the foreign materials as compared to the tobacco and which absorb all other wavelengths. The effect of this is to greatly reduce the noise in the electronic signal from the detector.

According to the present invention, a detectable taggant compound is added to the various lubricants used in manufacturing and processing machinery and, advantageously, taggant compounds having different characteristics are added into the lubricants at different processing locations, such that detection of one or more of these taggant compounds can enable rapid identification of the location of the source of lubricant contamination in the manufactured product.

Advantageously, the taggant compound is one which is detectable by fluorescence when it is exposed to particular wavelengths of light. In particular, a suitable taggant is one which absorbs energy at one wavelength and fluoresces/emits at a different wavelength. Such materials are well-known in the art as Stokes-shifting materials, and have recently found increasing use in inks for security marking of documents, such as banknotes and the like, to render such documents less susceptible to counterfeiting or copying. However, some conventional Stokes-shifting and anti-Stokes conversion materials are composed of inorganic compounds, such as doped rare earth metal particles, such as those described in U.S. Published Patent Application No. 2010/0219377, which are insoluble in lubricants. It would be advantageous if taggant compounds could be formulated to be soluble or dispersible in oils or lubricants.

In one form, the taggant may be an organic compound comprised of purified crystals from naturally occurring chlorophyll. Suitable naturally-occurring chlorophyll crystals include Chlorophyll A (CAS number 1406-65-1) and Chlorophyll B (CAS number 519-62-0). These taggants are known as being down-converting or fluorescent, and are sensitive to a particular narrow wavelength of IR light (680 nanometers). The taggant emits back this particular of light at a different wavelength (715 nanometers). A similar compound may be a benze-indolium perchlorate or a benze-indolium tosolyate. Such materials absorb around 670 nanometers and emit at a wavelength of 713 nanometers. Another material with down-conversion properties is Indocyanine Green (ICG).

The chemical structure for Chlorophyll A is provided below.

Chlorophyll a

Since this compound is an organic chemical, it is readily dissolved in oils and lubricants.

In another form, an oil-soluble fluorescent material has been developed based on Indocyanine Green (ICG), the chemical structure of which is provided below.

Indocyanine Green

Figure 3:
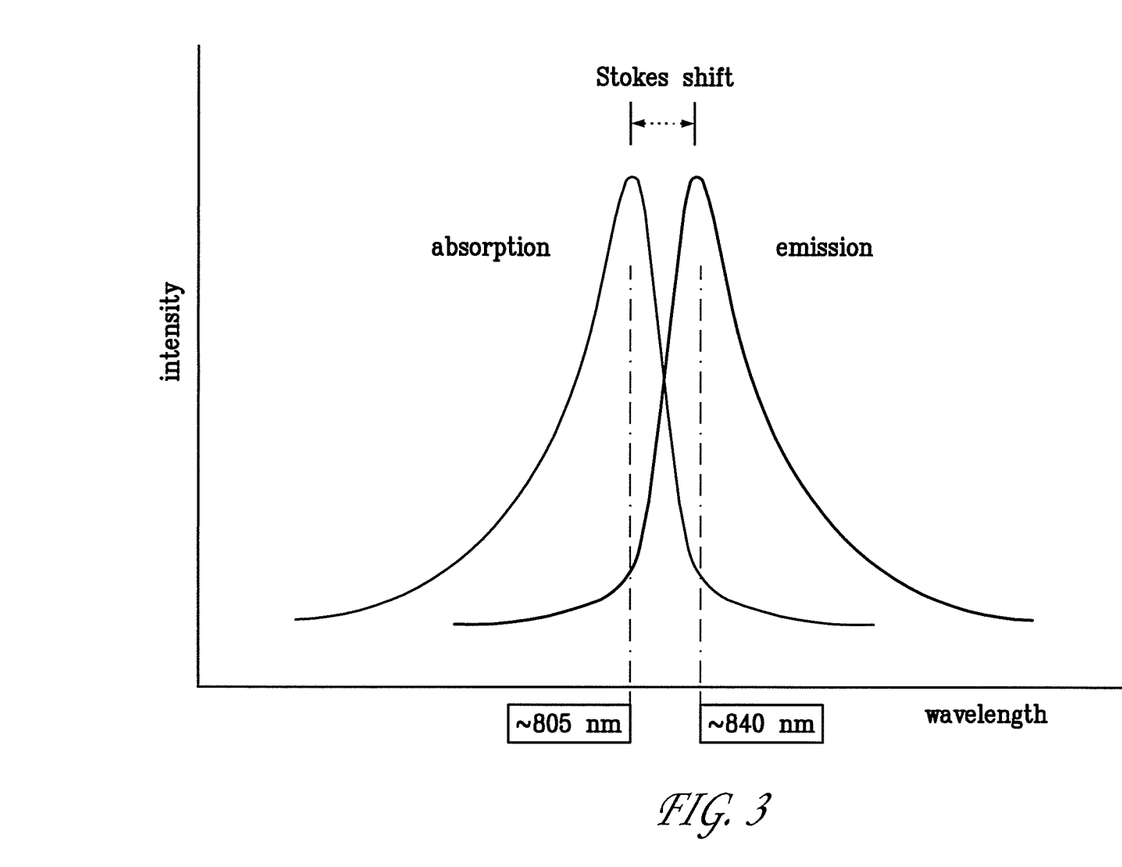
FIG. 3 is a representation of the infrared absorption and emission peaks of the Indocyanine Green (ICG) complex taggant, illustrating the Stokes-shift.

The new ICG-complex is sensitive to a particular narrow absorption band of IR light between about 760 to about 810 nanometers (FIG. 5), and emits light at a different band between about 810 to about 840 nanometers (FIG. 6), with discrete absorbance peaks at about 785 nanometers (FIG. 6) and 805 nanometers (FIG. 3), and a discrete emission peak at about 840 nanometers (FIG. 3).

The ICG complex can be added to oils or lubricants in the amounts of approximately 1 ppb to 5%, preferably a range of 1 ppm to 2000 ppm, based on the weight of the lubricant.

Figure 4:
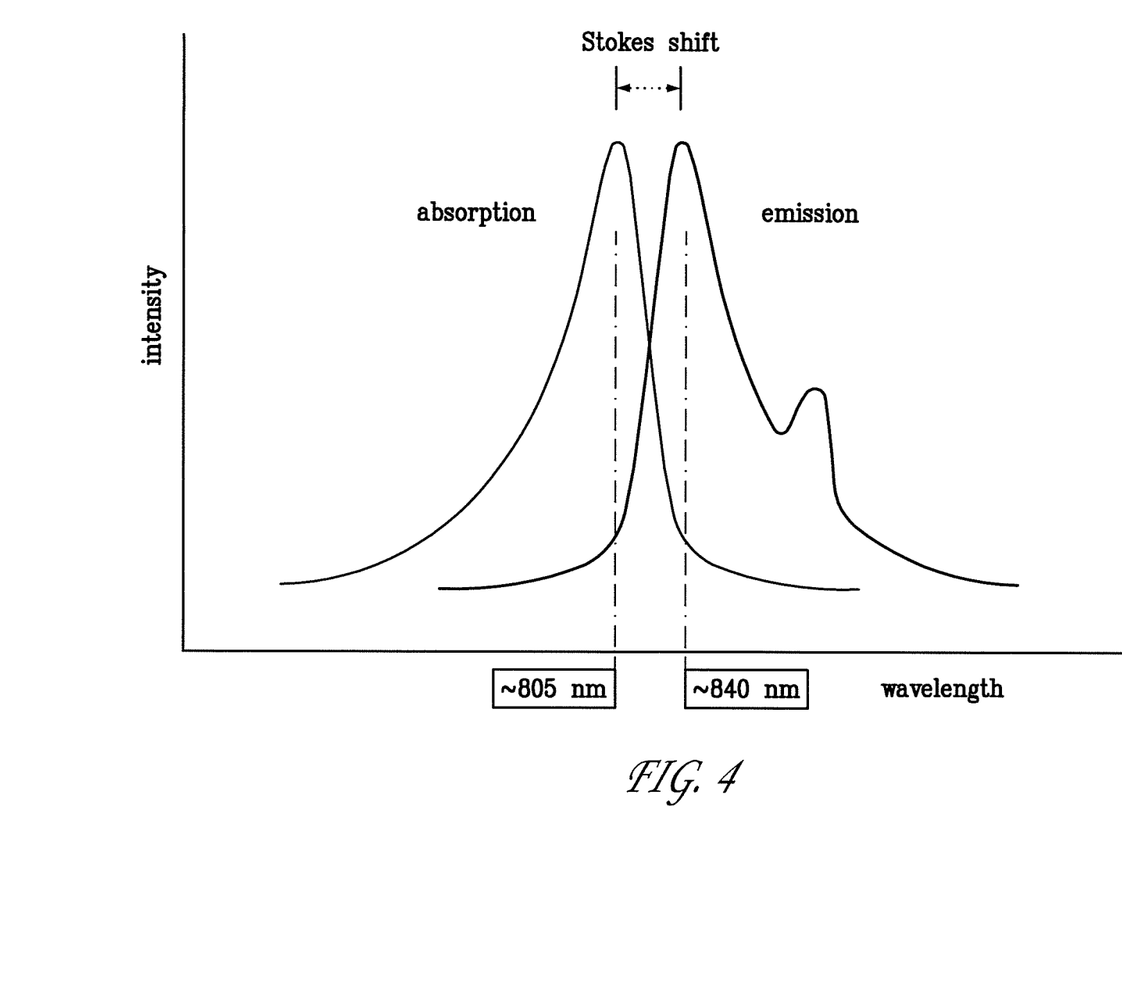
FIG. 4 is a representation of the infrared absorption and emission peaks of a modified ICG-complex, illustrating a secondary emission peak.
Figure 5:
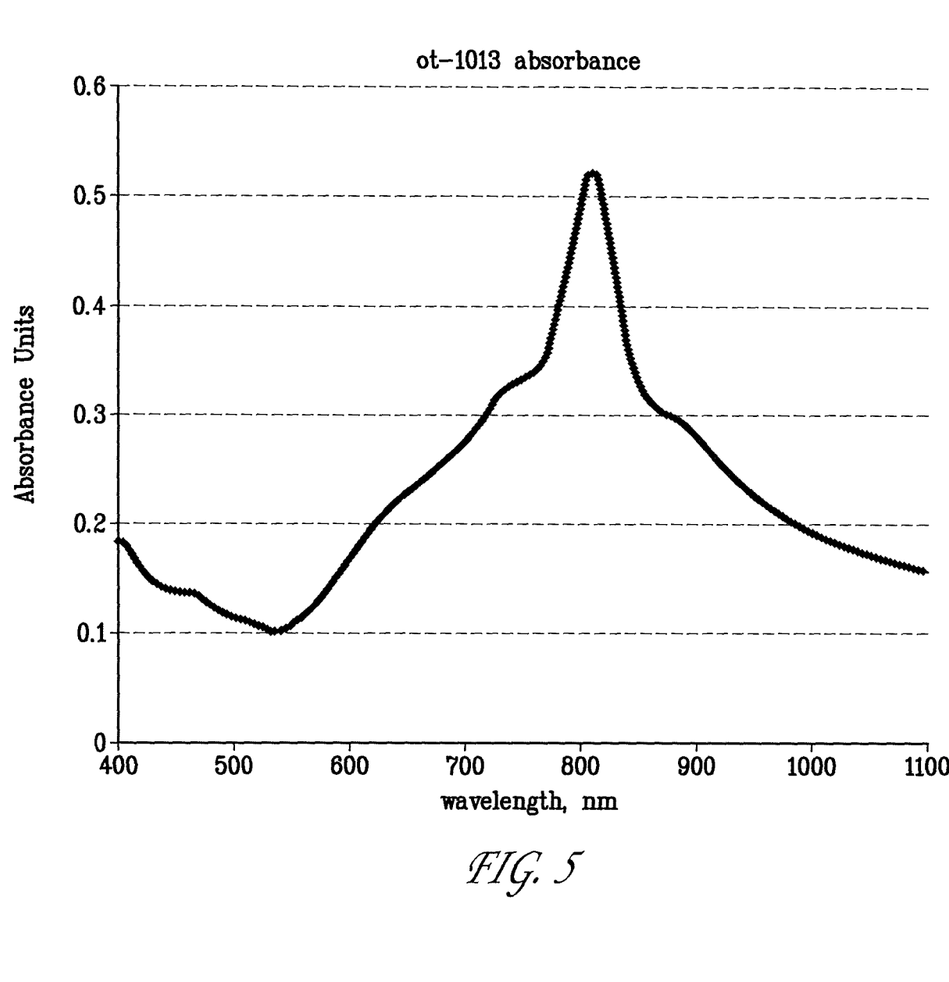
FIG. 5 is a representation of the infrared absorption peak for the modified ICG-complex of Example 1.
Figure 6:
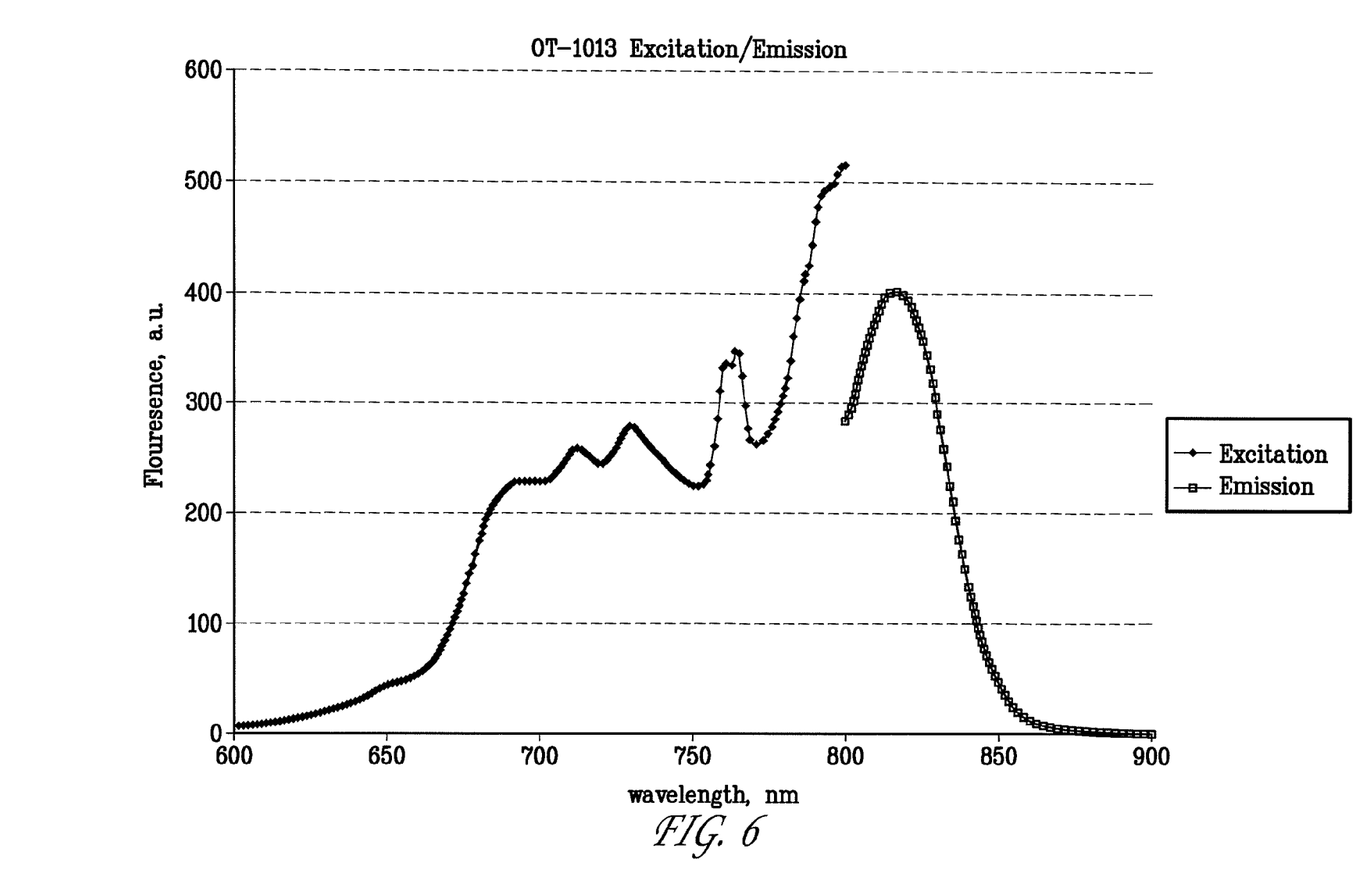
FIG. 6 is a representation of the infrared excitation and emission peaks for the modified ICG-complex of Example 1.

Additionally, the nature of the ICG complexing agent can be modified to impart one or more secondary NIR emission wavelengths adjacent to the major emission peak at 840 nanometers. By utilizing such variations in the complexing agent, and adding differently complexed ICG compounds in lubricants at differing locations in the overall process, a single detector can be located at the end of the process, and when contamination is detected, the contaminated product can be removed from the process and further analyzed for the secondary NIR emission peaks, to determine the location of the source of contamination. FIG. 4 is an illustration of the absorption and emission peaks of a modified ICG-complex, showing a secondary emission peak of a longer wavelength on the shoulder of the primary emission peak.

The present detection system utilizes near-infrared (NIR) emission, wherein a high intensity IR light source is directed at tobacco products and emitted IR light from the taggant is gathered and analyzed using a high speed NIR spectrometer sensor tuned to detect the emission signal from the particular taggant added to the oil. Adequate measures are made to prevent the detector from being able to see the excitation wavelength. This is done through the use of proper filters placed over the detectors. The light from the laser is pulsed at a frequency of about 800 Hz and the detector is inversely pulsed to detect the taggant. NIR light can penetrate into various materials, such as tobacco rods, to a depth of several millimeters, even enabling subsurface inspection of finished cigarettes. The high speed NIR sensor can detect tagged oils/lubricants at speeds of over about 2,000 feet per minute or 4,000 feet per minute or more.

The high-speed detector comprises an IR laser diode that is used to excite the taggant at its "absorption" frequency and a sensor that is tuned to receive light at the taggant's "emission" frequency. If the sensor detects the presence of the taggant, it can change the state of its output contacts. These output contacts can be used to stop the manufacturing equipment and set an alarm and/or to reject the oil contaminated product.

The taggant can be added to process machinery lubricants at concentrations between about 10 ppm and 100 ppm, typically at a concentration of about 50 ppm, based on the weight of the oil/lubricant. At these taggant concentration levels the detection system can detect as little as 10 microliters of oil, or even as little as 1 microliter of tagged oil.

However, in order to provide for easier treatment of oils or lubricants already in place within various machines, it can be more convenient to formulate a master batch of the taggant in any particular oil, wherein the taggant is mixed at higher concentrations in the base oil/lubricant, such as from about 0.1 to about 5 wt % taggant, or even from about 0.2 to about 2 wt % taggant, in a balance of the base oil/lubricant. A portion of such tagged master batch is then easily transported and added to oils/lubricants which are already in place in the machines to be treated, for example by adding a small amount of the tagged master batch to the oil sump of the machine.

When the taggant is not an oil-soluble taggant, such as when it is an inorganic particle, an optional surfactant or dispersant additive can be added in an amount effective to facilitate dispersion of the taggant particles in the base oil. Such surfactants/dispersants are well-known in the art and their identities need not be repeated herein.

A signal received by an NIR detector at a known location will indicate oil contamination in the processed material almost immediately, readily indicating the location of the source of contamination directly upstream of the detector.

In an alternative form, the nature of the ICG complexing agent can be modified to impart one or more secondary NIR emission wavelengths adjacent to the major wavelength peak at 840 nanometers. By utilizing such variations in the complexing agent, and adding differently complexed ICG compounds in lubricants at differing locations in the overall process, a single detector can be used, and when contamination is detected, the contaminated product can be removed from the process and further analyzed for the secondary NIR emission peaks, to determine the location of the source of contamination.

FIG. 3 is an illustration of the absorption and emission peaks of the presently disclosed ICG-complex taggant, and FIG. 4 an illustration of the absorption and emission peaks of a modified ICG-complex, showing a secondary emission peak of a longer wavelength on the shoulder of the primary emission peak.

In one form, when the NIR detection device detects the presence of the taggant primary emission peak, the identified product material is rejected and ejected from the system. Subsequent to ejection, the material can be re-analyzed with another NIR detection device which can identify the secondary wavelength peaks from any of the variety of differently-complexed ICG taggants, so as to determine the source of lubricant contamination throughout the system.

In another form, a method for removing oil contaminated product and foreign matter within a product stream is contemplated and provided herein. The method includes the steps of adding a fluorescent taggant to oil or lubricant contained in at least one processing machine; conveying a product stream that has been processed by the at least one processing machine; irradiating the conveyed product stream with infrared radiation; detecting infrared radiation emitted from the irradiated product stream due to the presence of the fluorescent taggant and generating a first signal in response thereto; illuminating the conveyed product stream; detecting light reflected from the illuminated product stream; comparing the light reflected from the illuminated product stream with light that would be expected to be reflected from an illuminated product stream free of foreign matter, and generating a second signal when the reflected light indicates the presence of foreign matter; and removing a portion of the conveyed product stream in response to the first or second signal.

It is envisioned that if a plurality of machines are involved to produce a raw material, then a plurality of taggants would be utilized individually as to each of them. Likewise, if a plurality of machines is involved to produce the final product, then a plurality of taggants would also be utilized individually as to each of them.

Specific forms will now be described further by way of example. While the following examples demonstrate certain forms of the subject matter disclosed herein, they are not to be interpreted as limiting the scope thereof, but rather as contributing to a complete description.

EXAMPLES

Example 1

500 mg of complexed ICG (Product No. OT-1013, available from Persis Science LLC of Andreas Pa.) is dispersed into 1.0 kg of Klüberoil 68 using a speedmixer. Klüberoil 68 is available from Klüber Lubrication North America L.P., Londonderry, N.H. The material is mixed for 10.0 minutes at a speed of 2100 RPM. The resulting concentrate is slowly added to an additional 100.0 kg of Kluberoil 68 while stirring under high speed dispersion. A sample of the material is placed into a Shimadzu 5301 Fluorometer and the excitation and emission spectrographs are recorded. When excited at a wavelength of 785, a strong infrared emission is noted from 810 nanometers to 960 nanometers. See FIG. 5 for a representation of the infrared absorption peak for the modified ICG-complex of Example 1 and FIG. 6 for a representation of the infrared excitation and emission peaks for the modified ICG-complex of Example 1.

Example 2

The above example is modified slightly using a tetrabutylammonium bromide complexation of an Infrared dye available, IR830 available from Sigma-Aldrich of St. Louis, Mo. After mixing, it is noted that the material will produce fluorescence around 833 nanometers when excited with approximately 0.5 mW of 785 light.

Example 3

Upconverting nanoparticles, MED C-19 ($Yb_2O_3:Er^{3+}$), were obtained from Persis Science, LLC in a slurry format in DMSO. The DMSO was dialyzed from the aqueous phase leaving the particles in aqueous phase. The particles were dried and dispersed into Kluberoil 68 using a Speedmixer. The dispersion was measured optically using a Spex Fluorolog-3. The oil suspension was excited at 970 nm and the detection occurred in the visible from 400 to 700 nm to determine the presence of the tagged oil.

Example 4

0.5 wt % of a europium chelate, available from Honeywell Corporation under the trade name of CD-335, was incorporated into 99.5 wt % of Lubriplate 220 oil using a horizontal media mill. Adequate detection was achieved using UV LED's at a wavelength of 363 nm and an APD detector with a 600 nm-700 nm notch filter.

Example 5

1.0 wt % of an infrared absorbing dithiolene dye commercially available from Epolin, Inc—358 Adams St. Newark N.J. 07105, was dissolved via mixing with 99 parts of Kluber Oil 220 under nitrogen with a stir bar for 5 hours. The resulting mixture was analyzed for infrared absorption. The absorption occurred from 800 nm to 1200 nm with a peak at around 1060 nm. The detection was achieved by contrast imaging with a Cognex In-Sight vision system and using a Monster LED light system with a wavelength of 850 nm. A Midwest optical filter 850 bandpass was used to isolate the absorption.

As may be appreciated, other tobacco- and non-tobacco-related consumer product applications can benefit from the invention disclosed herein. Contemplated tobacco-related applications include cigars, cigarillos, MST, pouched tobacco products. dry snuff, chewing tobacco and snus. The taggants disclosed herein may be applied in accordance with these teachings to various machines and machine modules that execute various manufacturing operations at points along the manufacturing process of interest. The systems and methods disclosed herein can be modified for compatibility with such applications.

While the present invention has been described and illustrated by reference to particular forms, those of ordinary skill in the art will appreciate that the invention lends itself to variations not necessarily illustrated herein. For this reason, then, reference should be made solely to the appended claims for purposes of determining the true scope of the present invention.

I claim:

1. A method for removing oil contaminated product and foreign matter within a product stream, said method comprising the steps of:
    (a) adding a fluorescent taggant to oil or lubricant contained in at least one processing machine;
    (b) conveying a product stream that has been processed by the at least one processing machine;
    (c) irradiating the conveyed product stream with infrared radiation;
    (d) detecting infrared radiation emitted from the irradiated product stream due to the presence of the fluorescent taggant and generating a first signal in response thereto;
    (e) illuminating the conveyed product stream;
    (f) detecting light reflected from the illuminated product stream;
    (g) comparing the light reflected from the illuminated product stream with light that would be expected to be reflected from an illuminated product stream free of foreign matter, and generating a second signal when the reflected light indicates the presence of foreign matter; and
    (h) removing a portion of the conveyed product stream in response to the first or second signal.

2. The method of claim 1, further including the step of causing the product stream to fall under the influence of gravity in a cascade.

3. The method of claim 2, wherein said step of removing a portion of the conveyed product stream in response to the first or second signal further includes directing fluid under pressure at a portion of the product stream.

4. The method of claim 3, wherein the fluid is a gas.

5. The method of claim 4, wherein the gas is air.

6. The method of claim 1, wherein the taggant is a Stokes-shifting taggant that absorbs infrared radiation at a first wavelength and fluoresces at a second wavelength, different from the first wavelength.

7. The method of claim 6, wherein the first wavelength is about 805 nanometers and the second wavelength is about 840 nanometers.

8. The method of claim 1, wherein the product stream comprises tobacco.

9. The method of claim 1, wherein the product stream comprises food products.

10. The method of claim 1, wherein the taggant is oil soluble.

* * * * *